(12) United States Patent
Origo

(10) Patent No.: US 10,543,153 B2
(45) Date of Patent: Jan. 28, 2020

(54) COSMETICS MADE IN ONE OR MORE COLOURS BY APPLYING A MAGNETIC FIELD, AND METHOD FOR THEIR PREPARATION

(71) Applicant: Art Cosmetics S.R.L., Mozzanica (BG) (IT)

(72) Inventor: Piero Origo, Mozzanica (IT)

(73) Assignee: ART COSMETICS S.R.L., Mozzanica (BG) (IT)

( * ) Notice: Subject to any disclaimer, the term of this patent is extended or adjusted under 35 U.S.C. 154(b) by 182 days.

(21) Appl. No.: 15/302,579

(22) PCT Filed: Apr. 8, 2015

(86) PCT No.: PCT/EP2015/057600
§ 371 (c)(1),
(2) Date: Oct. 7, 2016

(87) PCT Pub. No.: WO2015/155227
PCT Pub. Date: Oct. 15, 2015

(65) Prior Publication Data
US 2017/0027826 A1  Feb. 2, 2017

(30) Foreign Application Priority Data
Apr. 9, 2014  (IT) .............................. MI2014A0666

(51) Int. Cl.
*A61Q 1/12* (2006.01)
*A61K 8/26* (2006.01)
*A61Q 1/04* (2006.01)
*A61Q 1/10* (2006.01)
*A61K 8/19* (2006.01)

(52) U.S. Cl.
CPC .................. *A61K 8/26* (2013.01); *A61K 8/19* (2013.01); *A61Q 1/04* (2013.01); *A61Q 1/10* (2013.01); *A61K 2800/43* (2013.01); *A61K 2800/47* (2013.01); *A61K 2800/87* (2013.01)

(58) Field of Classification Search
None
See application file for complete search history.

(56) References Cited

U.S. PATENT DOCUMENTS

| 6,007,846 A | 12/1999 | Klar | |
| 7,678,449 B2 * | 3/2010 | Jones | C01G 49/0018 427/215 |
| 2009/0081261 A1 * | 3/2009 | Thevenet | A61K 8/19 424/401 |
| 2011/0000498 A1 * | 1/2011 | Tranchant | A45D 40/265 132/200 |
| 2011/0061675 A1 * | 3/2011 | McKinley | A45D 33/20 132/296 |

FOREIGN PATENT DOCUMENTS

| EP | 1700534 A1 | 9/2006 | |
| FR | 2888115 A1 | 1/2007 | |
| WO | WO-2004105708 A1 * | 12/2004 | A61K 8/02 |
| WO | 2006037901 A1 | 4/2006 | |
| WO | WO-2007032937 A1 * | 3/2007 | A61K 8/042 |
| WO | 2013104619 A1 | 7/2013 | |
| WO | WO-2013104619 A1 * | 7/2013 | A61Q 1/06 |
| WO | WO-2014108303 A1 * | 7/2014 | B05D 3/20 |

OTHER PUBLICATIONS

Serway, Jewett; "Physics for Scientists and Engineers, 6th ed." (2004), Thompson, pp. 946-950.*
Stablein; "Ferromagnetic Materials, vol. 3, Chapter 7, 'Hard Ferrites and Plastoferrites'," 1982; North-Holland Publising Co., pp. 441-602.*
International Preliminary Report on Patentability of PCT/EP2015/057600 dated Jun. 21, 2016.
Search Report and Written Opinion of PCT/EP2015/057600 dated Jun. 1, 2015.

* cited by examiner

*Primary Examiner* — Devang K Thakor
*Assistant Examiner* — Ivan A Greene
(74) *Attorney, Agent, or Firm* — Silvia Salvadori, P.C.; Silvia Salvadori

(57) ABSTRACT

The present invention relates to a cosmetic product having a visible pattern consisting of one or more colours, comprising a cosmetic composition including one or more dyes and/or pigments which contain magnetic or magnetisable particles, characterised in that said cosmetic composition is housed in a container enclosing a magnet capable of generating a magnetic field, whereby said dyes and/or pigments are positioned and/or oriented in the container by said magnetic field, thereby creating the visible pattern.

9 Claims, No Drawings

COSMETICS MADE IN ONE OR MORE COLOURS BY APPLYING A MAGNETIC FIELD, AND METHOD FOR THEIR PREPARATION

This application is a U.S. national stage of PCT/EP2015/057600 filed on 8 Apr. 2015, which claims priority to and the benefit of Italian Application No. MI2014A000666 filed on 9 Apr. 2014, the contents of which are incorporated herein by reference in their entireties.

FIELD OF INVENTION

The present invention relates to cosmetic products, preferably used for make-up, made in one or more colours with geometrical or random patterns housed in a container including a magnet.

TECHNICAL BACKGROUND

Numerous patent applications disclose the manufacture of make-up cosmetics in a plurality of colours, housed in a single container, using a variety of technologies. Some examples are patent applications JP2013079202, US2011073125, JP2012065847, US2008261844 and US2008277827. Said documents disclose technologies for the manufacture of multicoloured cosmetics in a single container in the form of a solid, powder, cast, fluid or emulsified product. However, a number of difficulties are involved in the manufacture of these cosmetics. The main technical difficulties include problems associated with making clear demarcations between the various colours, and the difficulty of combining in the same container colours that present physical incompatibilities with one another from the formulation standpoint, such as a colour in powder form and a colour in fluid form.

According to the literature, the manufacture of cosmetics with a plurality of colours in the same container requires the use, at least at one stage of the manufacturing process, of moulds, templates or preforms to prepare an initial rough pattern of the individual colours before combining them in the final container; however, this operation requires the use of complex machinery and equipment.

The use of magnetic fields applied to make-up cosmetics is also reported in the literature.

US 2011/000498 discloses a device for applying a cosmetic composition, in particular mascara, including a magnet and magnetic or magnetisable particles. The disclosed device makes it easier both to apply the composition and to improve the deposition of magnetic or magnetisable particles on keratinous fibres in order to obtain the visual effect created by magnetic particles having an optical effect by reflecting and/or diffracting light.

EP1700534 discloses an article having a film comprising magnetic particles oriented as a visible pattern, and an adhesive surface which assures the fixation of the article on the skin, fingernail or artificial fingernail. A magnetic field is applied during the manufacturing process of the article before drying the film.

FR2888115 discloses a liquid foundation including at least one colouring agent having non-zero magnetic susceptibility, such as metallic iron, preferably soft iron. The foundation is applied to the skin and then subjected to a magnetic field in order to modify the orientation of at least some of the particles of the colouring agent(s) presenting non-zero magnetic susceptibility.

WO2006/037901 discloses a kit for applying make-up to a surface such as the skin, nails, hair or lips, said kit comprising a first cosmetic composition including magnetic particles that are movable under the effect of a magnetic field and a second cosmetic composition for covering or being covered by the first composition and a magnetic device for generating a magnetic field that makes it possible to displace and/or modify the orientation of all or some of the magnetic particles when the first composition is applied in the form of a layer to the surface.

All of said patents disclose inventions relating to mainly fluid cosmetics which are first subjected, during or after application, to a magnetic field, in order to improve their cosmetic performance.

DESCRIPTION OF THE INVENTION

The present invention relates to the manufacture of cosmetics in one or more colours housed in a single container, which is also the final container designed for use. The colours may be visibly separated from one another without the use of moulds, templates or preforms, but with the use of a magnet applied directly to the container of the cosmetic product. Alternatively a decorative pattern is created in a monocolor cosmetic products by changing the orientation of the magnetic particles with the use of a magnetic field.

The subject of the present invention is a cosmetic product having a visible pattern consisting of one or more colours, comprising a cosmetic composition including one or more dyes and/or pigments which contain magnetic or magnetisable particles, characterised in that said cosmetic composition is housed in a container enclosing a magnet capable of generating a magnetic field, whereby said dyes and/or pigments are positioned and/or oriented in the container by said magnetic field, thereby creating the visible pattern.

In one embodiment of the invention the visible pattern consists of two or more colours forming coloured areas visibly separated from each other.

In a further embodiment of the invention, the visible pattern consists of one colour and said dyes and/or pigments, containing magnetic or magnetisable particles, are oriented in the container by said magnetic field, thereby creating the visible pattern.

The magnet can be applied internally or externally in contact with the container of the cosmetic composition.

The magnet generates a magnetic field with a magnetic induction value higher than 0.1 G ($10^{-5}$ T), a magnetic field intensity higher than 0.1 Oersted, and a magnetic permeability value higher than 0.1 MegaGauss Oersted.

The magnetic induction value preferably ranges between 2 G ($2 \times 10^{-4}$ T) and 3 G ($3 \times 10^{-4}$ T).

The intensity of the magnetic field preferably ranges between 2 Oe (0.16 kA/m) and 2.5 Oe (0.20 kA/m).

The magnetic permeability preferably ranges between 1.5 MGOe (11.94 KJ/$m^3$) and 2 MGOe (15.91 kJ/$m^3$).

The magnet preferably consists of magnetised plastoferrite, such as anisotropic magnetic rubber sold by Alga. The plastoferrite is preferably magnetised by inductive discharge to create a specific pattern. The magnet applied to the container positions and/or orients the dyes and/or pigments according to the specific design, creating a decorative effect without the use of moulds, templates or preforms.

The container can be made, for example, of glass, plastic, metal, natural fibres, synthetic fibres, non-woven fabric or a mixture thereof.

The dye and/or pigment is a dye and/or pigment acceptable for cosmetic use, and is preferably pearly.

According to the present invention, the term pearly dye and/or pigment means a luster particle (creating unique luster effects) that can be based on different substrates, for example mica (mica can be a natural or synthetic substrate), synthetic fluorphlogopite, silica, calcium aluminium borosilicate, calcium sodium borosilicate, aluminium calcium sodium silicate, acrylates copolymer, triethoxycaprylylsilane, polyurethane-11 and polyester (a polyester-based dye and/or pigment may be a glitter).

The particles orientable in a magnetic field preferably consist of at least one iron oxide or hydroxide.

The cosmetic compositions can be in solid, liquid or fluid form, and preferably take the form of a free or compact powder, waxy mass, liquid, paste, extruded product or emulsion.

Example 1: Manufacture of a Three-Colour Eye Make-Up Powder

The raw materials in the percentages by weight listed below:

| | |
|---|---|
| Talc | 2% |
| Mica CI 77019 | 5% |
| Titanium dioxide | 3% |
| Black iron oxide CI 77499 | 40% |
| Red iron oxide CI 77491 | 36.5% |
| FD&C blue no. 1 | 10% |
| Magnesium and aluminium silicate | 3% |
| Sorbic acid | 0.25% |
| Potassium sorbate | 0.25% | are mixed together in a fan grinder and divided by a powder filling machine between the final containers, to which a magnetic field with a magnetic induction value of 2.55 Gauss ($2.55 \times 10^{-4}$ T), a magnetic field intensity of 2.15 Oersted (0.17 kA/m) and magnetic permeability of 1.57 MGOe (12.49 kJ/m$^3$) is applied. The magnetic field to which the product is subjected visibly separates the colours contained in it. The orientation of the magnetic field in relation to the container determines the shape of the demarcation lines between the colours.

Example 2: Preparation of a Two-Colour Cast Lip Make-Up Product

The raw materials in the percentages by weight listed below:

| | |
|---|---|
| White beeswax | 1% |
| Ozokerite | 4% |
| Liquid paraffin | 0.5% |
| Castor oil | 30% |
| Titanium dioxide | 0.5% |
| Mica | 4% |
| Red iron oxide | 30% |
| Yellow iron oxide | 30% | are melted at the temperature of 90° C. in a wax melter. They are then divided by a fluid metering unit between the final containers, to which a magnetic field with a magnetic induction value of 2.40 Gauss ($2.40 \times 10^{-4}$ T), a magnetic field intensity of 2.35 Oersted (0.19 kA/m) and magnetic permeability of 1.45 MGOe (11.54 kJ/m$^3$) is applied. The magnetic field to which the product is subjected visibly separates the colours contained in it. The orientation of the magnetic field in relation to the container determines the shape of the demarcation lines between the colours.

The invention claimed is:

1. A cosmetic product having a decorative pattern consisting of one or more colours, comprising a cosmetic composition including one or more dyes and/or pigments which contain magnetic or magnetisable particles, wherein said cosmetic composition is housed in a container enclosing a magnet capable of generating a magnetic field, wherein said decorative pattern is made of said dyes and/or pigments positioned and/or oriented in the container by said magnetic field, wherein the cosmetic composition is in the form of a free powder.

2. The cosmetic product according to claim 1, wherein the decorative pattern consists of two or more colours forming colored areas separated from each other.

3. The cosmetic product according to claim 1, wherein the decorative pattern consists of one colour and said dyes and/or pigments are oriented in the container by said magnetic field, thereby creating the decorative pattern.

4. The cosmetic product according to claim 1, wherein the dye and/or pigment is a dye and/or pigment acceptable for cosmetic use.

5. The cosmetic product according to claim 4, wherein the dye and/or pigment is a pearly dye and/or pigment.

6. The cosmetic product according to claim 5, wherein the pearly dye or pigment is based on substrates selected from the group consisting of natural or synthetic mica, synthetic fluorphlogopite, silica, calcium aluminium borosilicate, calcium sodium borosilicate, aluminium calcium sodium silicate, acrylates copolymer, triethoxycaprylylsilane, polyurethane-11 and polyester.

7. The cosmetic product according to claim 1, wherein the magnetic or magnetisable particles consist of at least one iron oxide or hydroxide.

8. The cosmetic product according to claim 1, wherein the container consists of glass, plastic, metal, natural fibres, synthetic fibres, non-woven fabric or a mixture thereof.

9. The cosmetic product according to claim 1, wherein the magnet enclosed in said container generates a magnetic field with a magnetic induction value ranging between 2 G ($2 \times 10$-4 T) and 3 G ($3 \times 10$-4 T), an intensity of the magnetic field ranging between 2 Oe (0.16 kA/m) and 2.5 Oe (0.20 kA/m) and a magnetic permeability ranging between 1.5 MGOe (11.94 KJ/m3) and 2 MGOe (15.91 kJ/m3).

* * * * *